US009808656B2

United States Patent
Vinnakota et al.

(10) Patent No.: US 9,808,656 B2
(45) Date of Patent: Nov. 7, 2017

(54) SYSTEM AND METHOD OF OXYGEN DEFICIENCY WARNING IN A POWERED AIR PURIFYING RESPIRATOR

(75) Inventors: Vinay Kumar Vinnakota, Andhra Pradesh (IN); Praveen Kumar Palacharla, Andhra Pradesh (IN); Swapnil Gopal Patil, Maharashtra (IN)

(73) Assignee: Honeywell International Inc., Morris Plains, NJ (US)

(*) Notice: Subject to any disclaimer, the term of this patent is extended or adjusted under 35 U.S.C. 154(b) by 875 days.

(21) Appl. No.: 13/346,340

(22) Filed: Jan. 9, 2012

(65) Prior Publication Data

US 2013/0174845 A1 Jul. 11, 2013

(51) Int. Cl.
*A62B 18/00* (2006.01)
*A61M 16/06* (2006.01)
*A62B 9/00* (2006.01)

(52) U.S. Cl.
CPC ............ *A62B 18/006* (2013.01); *A62B 9/006* (2013.01); *A61M 16/06* (2013.01)

(58) Field of Classification Search
CPC .............. A61M 16/00; A61M 16/0066; A61M 2016/0021; A61M 16/0051; A61M 2205/33; A61M 2205/50; A61M 2205/58; A61M 2205/3303; A61M 2205/581; A61M 2205/582; A61M 2016/1025; A61M 2205/583; A61M 2205/18; A61M 2205/52; A62B 7/00; A62B 18/00; A62B 7/002; A62B 18/006; A62B 18/02; A62B 18/025; A62B 18/04; A62B 18/045
USPC ............ 128/201.22, 201.23, 201.24, 201.25, 128/201.26, 201.27, 201.28, 201.29, 128/202.11, 204.29, 204.22, 204.21, 128/204.18, 204.26, 200.24, 202.22, 128/205.23; 600/301
See application file for complete search history.

(56) References Cited

U.S. PATENT DOCUMENTS

| | | |
|---|---|---|
| 3,773,044 A | 11/1973 | Wallace |
| 3,965,892 A | 6/1976 | Colston et al. |
| 4,046,492 A | 9/1977 | Inglis |
| 4,088,461 A | 5/1978 | Brauer |

(Continued)

FOREIGN PATENT DOCUMENTS

| | | |
|---|---|---|
| DE | 102004013452 A1 | 10/2005 |
| EP | 0042736 A1 | 12/1981 |

(Continued)

OTHER PUBLICATIONS www.home-med-equip.com/catalog/invacare-perfecto2-v-oxygen-concentrator-with-senso2-irc5po2v.html; information sheet; 1 page.

(Continued)

*Primary Examiner* — Lynne Anderson
*Assistant Examiner* — Elliot S Ruddie
(74) *Attorney, Agent, or Firm* — Conley Rose, P.C (57) ABSTRACT

A powered air purifying respirator (PAPR). The PAPR comprises an electric motor mechanically coupled to a blower, an oxygen sensor, an alarm device, and a controller coupled to the oxygen sensor and to the electric motor, wherein the controller controls the electric motor, wherein the controller determines if the oxygen concentration is deficient, and wherein the controller commands the alarm device to present an indication when the oxygen concentration is deficient.

20 Claims, 3 Drawing Sheets

(56) References Cited

U.S. PATENT DOCUMENTS

| | | | |
|---|---|---|---|
| 4,109,509 A * | 8/1978 | Cramer et al. | 73/23.3 |
| 4,146,887 A | 3/1979 | Magnante | |
| 4,154,586 A | 5/1979 | Jones et al. | |
| 4,155,358 A | 5/1979 | McAllister et al. | |
| 4,195,780 A | 4/1980 | Inglis | |
| 4,326,514 A | 4/1982 | Eian | |
| 4,365,627 A | 12/1982 | Wing | |
| 4,385,728 A | 5/1983 | Inglis et al. | |
| 4,421,719 A | 12/1983 | Burleigh | |
| 4,530,706 A | 7/1985 | Jones | |
| 4,899,740 A | 2/1990 | Napolitano | |
| 4,905,687 A | 3/1990 | Ponkala | |
| 5,018,946 A | 5/1991 | Breckner et al. | |
| 5,253,640 A | 10/1993 | Falb et al. | |
| 5,255,412 A | 10/1993 | Mally et al. | |
| 5,285,794 A | 2/1994 | Lynch | |
| 5,297,544 A | 3/1994 | May et al. | |
| 5,413,097 A | 5/1995 | Birenheide et al. | |
| 5,512,882 A | 4/1996 | Stetter et al. | |
| 5,577,496 A | 11/1996 | Blackwood et al. | |
| 5,659,296 A | 8/1997 | Debe et al. | |
| 5,671,730 A | 9/1997 | Olila | |
| 5,848,591 A | 12/1998 | Weismann | |
| 5,950,621 A | 9/1999 | Klockseth et al. | |
| 5,970,975 A | 10/1999 | Estes et al. | |
| 6,186,140 B1 | 2/2001 | Hoague | |
| 6,340,291 B1 | 1/2002 | Reckert | |
| 6,375,725 B1 | 4/2002 | Bernard et al. | |
| 6,401,714 B1 | 6/2002 | Giorgini | |
| 6,452,510 B1 * | 9/2002 | Zysko | 340/970 |
| 6,651,658 B1 * | 11/2003 | Hill et al. | 128/204.23 |
| 6,666,209 B2 | 12/2003 | Bennett et al. | |
| 6,701,864 B2 | 3/2004 | Watson, Jr. et al. | |
| 6,814,073 B2 | 11/2004 | Wickham | |
| 6,953,318 B2 | 10/2005 | Krugerke | |
| 7,195,015 B2 | 3/2007 | Kuriyama | |
| 7,236,818 B2 | 6/2007 | McLeod et al. | |
| 7,296,573 B2 | 11/2007 | Estes et al. | |
| 7,328,700 B2 | 2/2008 | Baker et al. | |
| 7,380,551 B2 | 6/2008 | Alvey | |
| 7,442,237 B1 | 10/2008 | Gardner | |
| 7,503,962 B2 | 3/2009 | Attar | |
| 7,798,017 B2 | 9/2010 | Betz | |
| 7,897,109 B2 | 3/2011 | Labuda et al. | |
| 9,192,795 B2 | 11/2015 | Palacharla et al. | |
| 2002/0062830 A1 | 5/2002 | Meier et al. | |
| 2002/0139370 A1 | 10/2002 | Bachinski | |
| 2003/0019494 A1 | 1/2003 | Bennett et al. | |
| 2003/0192536 A1 | 10/2003 | Odell et al. | |
| 2003/0223877 A1 | 12/2003 | Anstine et al. | |
| 2004/0223876 A1 | 11/2004 | Kirollos et al. | |
| 2005/0005935 A1 | 1/2005 | Gradon | |
| 2005/0022817 A1 * | 2/2005 | Alvey | A62B 7/02 128/205.22 |
| 2005/0109341 A1 | 5/2005 | Alvey | |
| 2005/0115561 A1 * | 6/2005 | Stahmann et al. | 128/200.24 |
| 2005/0183721 A1 | 8/2005 | Juergensen | |
| 2006/0213513 A1 | 9/2006 | Seong | |
| 2007/0163588 A1 | 7/2007 | Hebrank et al. | |
| 2007/0215159 A1 | 9/2007 | Ross et al. | |
| 2007/0235030 A1 | 10/2007 | Teetzel et al. | |
| 2008/0063575 A1 | 3/2008 | Rakow et al. | |
| 2008/0092891 A1 | 4/2008 | Cewers | |
| 2008/0216833 A1 | 9/2008 | Pujol et al. | |
| 2009/0004047 A1 | 1/2009 | Hunter et al. | |
| 2009/0027216 A1 * | 1/2009 | Huang et al. | 340/632 |
| 2009/0266361 A1 | 10/2009 | Bilger et al. | |
| 2011/0114093 A1 | 5/2011 | Patil et al. | |
| 2011/0114094 A1 | 5/2011 | Stone et al. | |
| 2011/0146682 A1 | 6/2011 | Patil et al. | |
| 2011/0162647 A1 | 7/2011 | Huby et al. | |
| 2012/0084053 A1 * | 4/2012 | Yuen | A61B 5/0002 702/160 |
| 2012/0138051 A1 * | 6/2012 | Curran et al. | 128/201.25 |
| 2014/0190483 A1 * | 7/2014 | Hansen et al. | 128/205.12 |

FOREIGN PATENT DOCUMENTS

| | | |
|---|---|---|
| EP | 1417988 A1 | 12/2004 |
| EP | 2070563 A1 | 6/2009 |
| EP | 2591827 A2 | 5/2013 |
| GB | 1597979 | 12/1977 |
| GB | 1554542 | 1/1978 |
| GB | 2180761 A | 4/1987 |
| GB | 2209474 A | 5/1989 |
| GB | 2287656 A | 9/1995 |
| GB | 2472592 A | 2/2011 |
| JP | 2009178427 A | 8/2009 |
| WO | 9612523 | 5/1996 |
| WO | 9629116 A1 | 9/1996 |
| WO | 9927352 | 6/1999 |
| WO | 0143827 A1 | 6/2001 |
| WO | 03028842 A2 | 4/2003 |
| WO | 2007128584 A1 | 11/2007 |
| WO | 2008006152 A1 | 1/2008 |
| WO | 2009067583 A2 | 5/2009 |

OTHER PUBLICATIONS

Utility U.S. Appl. No. 13/269,198; Honeywell File No. H0027769 entitled: System and Method of Calibration in a Powered Air Purifying Respirator, filed Oct. 7, 2011; 25 pages.
Toyotomi Air Purifier with Oxygen Concentrator Model ETK-S50DX; www.toyotomiusa.com; informaton sheet; 1 page.
Utility U.S. Appl. No. 13/269,198; Honeywell File No. H002779 entitled : System and Method of Calibration in a Powered Air Purifying Respirator, filed Oct. 7, 2011; 25 pages.
Toyotomi Air Purifyer with Oxygen Concentrator Model ETK-S50DX; www.toyotomiusa.com; information sheet; 1 page.
PCT/US2012/058508, PCT International Search Report, dated Dec. 18, 2013, 3 pages.
PCT/US2012/058508, PCT Written Opinion of the International Searching Authority, dated Dec. 18, 2013, 5 pages.
European Patent Application No. 13150193.4, European Search Report, dated Apr. 22, 2016, 4 pages.
European Patent Application No. 13150193.4, Examination Report, dated May 19, 2016, 8 pages.
International Patent Application No. PCT/US2012/058508, International Preliminary Report on Patentability, dated Apr. 8, 2014, 6 pages.
U.S. Appl. No. 13/269,198, Restriction Requirement, dated Apr. 4, 2014, 8 pages.
U.S. Appl. No. 13/269,198, Office Action, dated Jul. 9, 2014, 36 pages.
U.S. Appl. No. 13/269,198, Final Office Action, dated Oct. 9, 2014, 25 pages.
U.S. Appl. No. 13/269,198, Advisory Action, dated Dec. 9, 2014, 4 pages.
U.S. Appl. No. 13/269,198, Notice of Allowance, dated Jul. 10, 2015, 18 pages.
European Patent Application No. 13150193.4, Examination Report, dated Mar. 28, 2017, 38 pages.

* cited by examiner

SYSTEM AND METHOD OF OXYGEN DEFICIENCY WARNING IN A POWERED AIR PURIFYING RESPIRATOR

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Powered air purifying respirators (PAPRs) utilize a mechanism, such as a blower, impeller, fan or other mechanism, to draw ambient air through air purifying elements to remove contaminants from the air. PAPRs are designed to be human portable for use in atmospheres with solid and liquid contaminants, gases, and/or vapors to provide a useable and safe supply of breathable air where the concentrations of contaminants are not immediately dangerous to life or health and the atmosphere contains adequate oxygen to support life. PAPRs carry a self-contained power source such as a battery to energize a motor to drive the blower, impeller, or fan. The self-contained power source desirably is sized small enough so the PAPR is readily human portable and large enough that the PAPR can be used without recharging the power source for a portion of a work shift effective to promote efficient worker operation.

SUMMARY

In an embodiment, a powered air purifying respirator (PAPR) is disclosed. The PAPR comprises an electric motor mechanically coupled to a blower, an oxygen sensor, an alarm device, and a controller coupled to the oxygen sensor and to the electric motor, wherein the controller controls the electric motor, or, wherein the controller determines if the oxygen concentration is deficient, and wherein the controller commands the alarm device to present an indication when the oxygen concentration is deficient.

In an embodiment, a powered air purifying respirator (PAPR) is disclosed. The PAPR comprises an electric motor mechanically coupled to a blower, an oxygen sensor, an alarm device, an event store, and a controller coupled to the oxygen sensor, to the alarm device, to the event store, and to the electric motor. The controller controls the electric motor, wherein the controller receives an indication of an oxygen concentration from the oxygen sensor, wherein the controller determines if the oxygen concentration is deficient based on the indication of the oxygen concentration, wherein the controller commands the alarm device to present an indication and writes a record in the event store when it determines the oxygen concentration is deficient.

In an embodiment, a method of operating a powered air purifying respirator (PAPR) is disclosed. The method comprises powering on the PAPR, receiving an indication of oxygen concentration by an electronic controller, determining that the oxygen concentration is below a pre-defined threshold by the electronic controller, and presenting an indication of oxygen concentration deficiency.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

Powered air purifying respirators (PAPRs) are well known in the art. An exemplary PAPR is described in US Patent Application Publication US 2011/0146682 A1 entitled "Sensor Apparatus and Method to Regulate Air Flow in a Powered Air Purifying Respirator" by Swapnil Gopal Patil et al., published Jun. 23, 2011, U.S. patent application Ser. No. 12/645,044 filed Dec. 22, 2009, which is hereby incorporated by reference for some embodiments herein to the extent that it is not inconsistent with and/or does not contradict information presented directly in the present disclosure. A PAPR may comprise a motor mechanically coupled to an air blower. As the motor turns the air blower, the air blower draws air through one or more filters and delivers breathable air to a user, for example via a hose to a face mask worn by the user. The PAPR may comprise a battery that provides power to drive the motor and a controller that regulates the speed of the motor to provide a controlled air flow rate.

PAPRs are intended for use in atmospheres that are not immediately dangerous to life or health (IDLH) and where the atmosphere contains adequate oxygen. Individuals breathing in oxygen deficient environments may experience symptoms such as headaches, ringing in the ears, dizziness, drowsiness, unconsciousness, nausea, vomiting, and depression of all the senses. Under some circumstances of excessive oxygen deficiency, death can occur. In working conditions having oxygen deficient atmosphere, a worker may be more likely to cause an accident injuring himself or herself, injuring another worker, damaging a work product, or damaging equipment. A worker using a PAPR may begin working in an atmosphere having an adequate oxygen concentration, but the atmosphere may change to have an oxygen deficiency. As used herein, the term oxygen concentration refers to the percent of the ambient gaseous atmosphere that is composed of breathable oxygen ($O_2$). The present disclosure teaches a PAPR having an oxygen sensor coupled to a controller that regulates the speed of the blower motor, wherein the controller also monitors the ambient oxygen concentration level. When an oxygen deficiency occurs, the controller commands a presentation device to present an alert and/or an alarm to the user of the PAPR. In an embodiment, the controller may also store an event record in an electronic memory for use in auditing the safety practices of a facility and/or for use in conducting an accident investigation.

Figure 1:
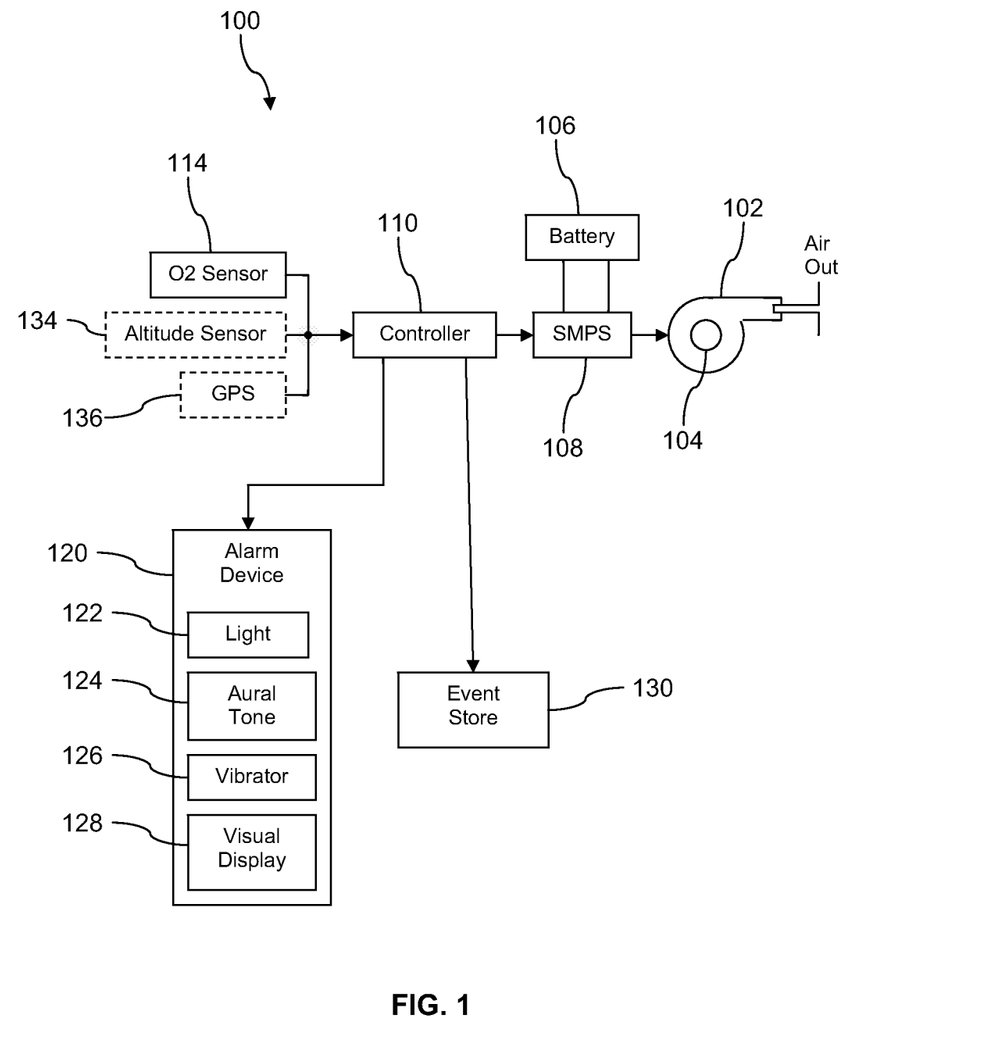
FIG. 1 is an illustration of a powered air purifying respirator according to an embodiment of the disclosure.

Turning now to FIG. 1, a PAPR 100 is described. In an embodiment, the PAPR 100 comprises an air blower 102, an electric motor 104, a battery 106, a switched mode power supply (SNIPS) 108, a controller 110, an oxygen sensor 114, and an alarm device 120. The electric motor 104 is mechanically coupled to the blower 102 to turn the blower 102 and to cause air to flow through a filter and to supply filtered air to a user of the PAPR 100. In an embodiment, the controller 110 may be an electronic controller or processor. Alternatively, the controller 110 may be an algorithm or firmware that is executed by a processor such as a microcontroller, a microprocessor, a digital signal processor (DSP), an application specific integrated circuit (ASIC), a field programmable gate array (FPGA), a complex programmable logic device (CPLD), or other processor. In some contexts the alarm device 120 may be referred to as a presentation device or an alerting device. It is understood that some components commonly present in PAPRs are not shown in FIG. 1 to avoid cluttering the illustration. For example, in an embodiment, the air outlet at the right hand side of the illustration may be coupled into an air hose attached to a face mask.

In an embodiment, the PAPR 100 may be varied in some ways, and some components may be combined. For example, in an embodiment, the PAPR 100 may not employ the switched mode power supply 108 but instead some other form of electrical power modulation component that modulates electrical power delivered to the electric motor 104 under control of the controller 110. In an embodiment, the controller 110 may comprise the circuitry for electrical power modulation and may connect directly to the electric motor 104. In an embodiment, the output of the oxygen sensor 114 may be filtered before feeding into the controller 110. For example, the output of the oxygen sensor 114 may be low-pass filtered to remove noise from the oxygen sensor signal.

The switched mode power supply 108 may deliver a pulsed width modulated electrical power output to the electric motor 104 that is characterized by a voltage amplitude and/or a pulse duration or width. By increasing the output pulse duration and/or pulse duty cycle of the switched mode power supply 108, the controller 110 indirectly commands the electric motor 104 to turn faster and hence to increase the rate of air flow delivered by the air blower 102. By decreasing the output pulse duration of the switched mode power supply 108, the controller 110 indirectly commands the electric motor 104 to turn slower and hence to decrease the rate of air flow delivered by the air blower 102. In an embodiment, the controller 110 may monitor air flow feedback to maintain the rate of air flow delivered by the air blower 102 approximately at a reference air flow level. For further information about determining rate of air flow delivered by the air blower 102, see U.S. patent application Ser. No. 12/618,940, filed Nov. 16, 2009, entitled "Automatic Fitment Detection and Flow Calibration Using Non-Contact Sensing Powered Air Purifying Respirators," by Swapnil Gopal Patil, et al., which is hereby incorporated by reference for some embodiments herein to the extent that it is not inconsistent with and/or does not contradict information presented directly in the present disclosure. For further information about the determination of an air flow reference level and modulating air flow delivered by the air blower 102, see U.S. patent application Ser. No. 13/269,198, filed Oct. 7, 2011, entitled "System and Method of Calibration in a Powered Air Purifying Respirator" by Praveen Kumar Palacharla, et al., which is hereby incorporated by reference for some embodiments herein to the extent that it is not inconsistent with and/or does not contradict information presented directly in the present disclosure.

The controller 110 is coupled to the oxygen sensor 114 and to the electric motor 104. The controller 110 monitors an indication of ambient oxygen concentration provided by the oxygen sensor 114 and compares the ambient oxygen concentration to a pre-determined oxygen deficiency threshold. In an embodiment, the oxygen deficiency threshold can be defined as a percent of the ambient gaseous atmosphere that is composed of breathable oxygen (O2), but in another embodiment the oxygen deficiency threshold may be defined in another manner. For example, in an embodiment, the pre-determined oxygen deficiency threshold may be 19.5%, where this percentage refers to the percent of the ambient gaseous atmosphere that is composed of breathable oxygen ($O_2$).

If the controller 110 determines that the ambient atmosphere has an oxygen concentration that falls below the pre-determined oxygen deficiency threshold, the controller 110 commands the alarm device 120 to present an indication of oxygen deficiency. In some contexts, the controller 110 may be said to determine if the oxygen concentration is deficient based on the indication of oxygen concentration provided by the oxygen sensor 114. In an embodiment, the alarm device 120 may comprise one or more of an indicator light 122 or light device, an aural tone generating device 124, a vibrator device 126, or a visual display device 128. The indicator light 122 may illuminate steadily or flash in an eye attracting sequence to alert the user of the PAPR 100 of an oxygen deficient atmosphere. The indicator light 122 may be an incandescent light, a light emitting diode (LED), or another illuminating device. The aural tone generating device 124 may emit any of a variety of aural sounds or ones, for example, a constant tone or combination of tones, a digitally recorded verbal message, a varying frequency audio alert, or other. The vibrator device 126 may vibrate continuously or vibrate for a duration of time interspersed with inactivity. The visual display 128 may present a text message and/or a graphical indication.

When the user of the PAPR 100 is notified by presentation of an alarm by the alarm device 120, the user may leave the area experiencing the deficiency of oxygen and move to a more oxygenated environment. This behavior, supported by the oxygen deficiency monitoring function of the PAPR 100 taught by the present disclosure, can contribute to increased safety in the workplace.

The PAPR 100 may further comprise an electronic event, store 130, and the controller 110 may write records into the event store 130 when an oxygen deficiency is determined. For example, the controller 110 may write a record of information about the oxygen deficiency event into an electrically programmable memory device. The record may comprise a date and time of the oxygen deficiency event. The record may comprise a numerical representation of the indication of oxygen concentration at the time the oxygen deficiency is determined. The record may comprise an identity of a user of the PAPR 100. The record may comprise other information as well. The controller 110 may write only a single record to the event store 130 for a single instance of oxygen deficiency, where the event may be defined to continue until the oxygen level returns above the predetermined level of oxygen deficiency. The controller 110 may update the single record, for example as the oxygen concentration indication input by the oxygen sensor 114 decreases, the controller 110 may update the single record to capture the extreme sensed value of the oxygen deficiency.

The controller 110 may also update the single record with a time duration of the oxygen deficiency, for example if the oxygen deficiency lasts for two minutes, the record may indicate an oxygen deficiency episode of two minutes. Alternatively, the controller 110 may generate a plurality of oxygen deficiency records on some periodic basis. This may promote later calculation of an integrated oxygen deficiency metric, where the magnitude of oxygen deficiency and the time duration of oxygen deficiency may be determined based on analyzing the plurality of records in the electronic event store 130. In some contexts the controller 110 may be said to be coupled to the event store 130. In an embodiment, the event, store 130 may be a separate memory chip. Alternatively, the event store 130 may be part of the controller 110.

In an embodiment, the determination of an oxygen deficiency event is based on both a sensed level of oxygen concentration and based on an altitude at which the PAPR 100 is used. For example, in an embodiment, thresholds of oxygen deficiency may be defined approximately as follows.

TABLE 1

Oxygen Deficiency Threshold Based on Altitude.

| Altitude range | O2 deficiency threshold |
|---|---|
| Less than 3,001 feet | 16.0% |
| 3,001 to 4,000 feet | 16.4% |
| 4,001 to 5,000 feet | 17.1% |
| 5,001 to 6,000 feet | 17.8% |
| 6,001 to 7,000 feet | 18.5% |
| 7,001 to 8,000 feet | 19.3% |
| Over 8,000 feet | 19.5% |

Thus, if operating in a location at an altitude of less than 3,001 feet, the controller 110 may determine that an oxygen concentration of about 16% is allowable while an oxygen concentration of less than 16% is an oxygen deficient environment, the controller 110 may command the alarm device 120 to present an alarm to the user of the PAPR 100, and the controller 110 may write a record to the event store 130. If operating in a location at an altitude of 5,500 feet, however, the controller 110 may determine that an oxygen concentration of less than 17.8% is an oxygen deficient environment, the controller 110 may command the alarm device 120 to present an alarm to the user of the PAPR 100, and the controller 110 may write a record to the event store 130. As used herein, the term oxygen concentration refers to the percent of the ambient gaseous atmosphere that is composed of breathable oxygen ($O_2$). It is understood that it is contemplated that different standards for oxygen deficiency may be defined for use by the controller 110 in determining oxygen deficiency conditions.

In an embodiment, the altitude at which the PAPR 100 is to be operated may be pre-configured into the PAPR 100, for example written into a read only memory (ROM) of the PAPR 100 at order fulfillment time. For example, as part of an ordering process, an industrial plant may need to specify what altitude the subject PAPR 100 will be used at, and then the appropriate altitude parameter may be stored in the PAPR 100. Alternatively, the PAIR 100 may have a user interface that promotes a user inputting and/or configuring the altitude at which the user is utilizing the PAPR 100. Alternatively, in an embodiment, the PAPR 100 may further comprise an altitude sensor 134 that provides an indication of the sensed altitude of the ambient atmosphere. Alternatively, in an embodiment, the PAPR 100 may further comprise a global positioning system (GPS) receiver 136 that is capable of determining an altitude of the PAPR 100 based on receiving and interpreting signals broadcast by global positioning satellites. The controller 110 may be said to be coupled to the altitude sensor 134 and/or coupled to the global positioning system receiver 136. Alternatively, the PAPR 100 may feature a radio receiver that receives an altitude parameter broadcast from a wireless access point proximate to the PAPR 100 and stores the broadcast altitude parameter for use by the controller 110 in determining whether an oxygen deficiency exists.

Figure 2:
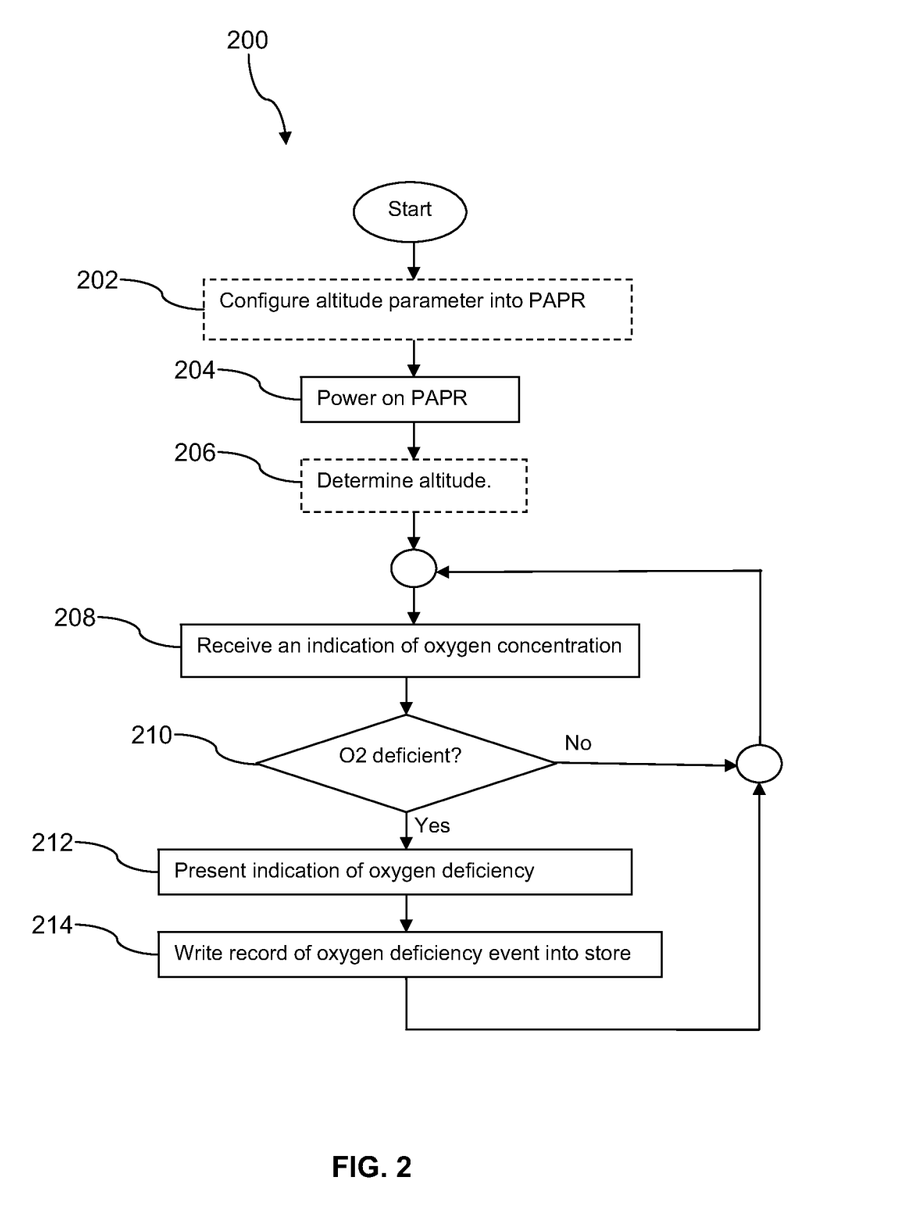
FIG. 2 is a flow chart of a method according to an embodiment of the disclosure.

Turning now to FIG. 2, a method 200 is described. At block 202, an anticipated operation altitude is optionally configured into the PAPR 100. For example, at an assembly plant, an altitude parameter is written into a storage area in the electronics of the PAPR 100, for example written into an electrically programmable memory coupled to the controller 110 or into a portion of the controller 110. Alternatively, the altitude parameter may be configured into the PAPR 100 at a use location, for example by an administrator or information technology specialist. Alternatively, the altitude parameter may be configured into the PAPR 100 each time.

At block 204, the PAPR 100 is powered on. In an embodiment, rather than in block 202, the altitude parameter may be configured into the PAPR 100 by a user after powering on the PAPR 100. At block 206, an altitude of the PAPR 100 is optionally automatically determined. In an embodiment, the altitude may be determined by the altitude sensor 134 and/or by the controller 110. In another embodiment, the altitude may be determined by the global positioning system receiver 136.

At block 208, an indication of oxygen concentration is received, for example the controller 110 receives an indication of oxygen concentration from the oxygen sensor 114. The controller 110 may filter or smooth the indication of oxygen concentration to remove sensor noise or other perturbations of the indication. At block 210, the oxygen concentration is compared to an oxygen deficiency threshold. In an embodiment, the oxygen deficiency threshold may be independent of altitude, for example, the oxygen deficiency threshold may be an oxygen concentration of 19.5% without reference to the altitude at which the PAPR 100 is operated. In another embodiment, however, the oxygen deficiency threshold may be indexed or determined by the altitude at which the PAPR 100 is operated, for example based on oxygen deficiency thresholds such as those defined in Table 1 presented above. If the oxygen concentration does not fall below the oxygen deficiency threshold, the processing returns to block 208. If the oxygen concentration falls below the oxygen deficiency threshold (thus, the oxygen concentration in the work environment is deficient), the processing proceeds to block 212.

At block 212, an indication of oxygen deficiency is presented. The presentation may comprise turning on or flashing the light 122, sounding an aural tone with the aural tone generator 124, vibrating by the vibrator 126, and/or presenting a visual indication by the visual display 128. At block 214, the controller 110 writes a record to the event store 130 about the oxygen deficiency event. In an embodiment, the controller 110 may write a single record to the event store 130 for one case of an oxygen deficient work environment. In this case, the controller 110 may determine that an oxygen deficiency event continues until the oxygen concentration increases above the oxygen threshold. Alternatively, the controller 110 may determine that the oxygen deficiency event continues until the oxygen concentration increases above the oxygen threshold and remains above the oxygen threshold for a predetermined period of time, for example for 10 seconds, for 1 minute, for 5 minutes, or for some other period of time effective to reduce toggling of oxygen deficiency events. Alternatively, the controller may determine that the oxygen deficiency event continues until the oxygen concentration increases above a second oxygen threshold, where the second oxygen threshold is greater than the oxygen deficiency threshold.

After block 214, the processing then returns to block 208. In an embodiment, the processing continually loops through blocks 208 and 210 or through blocks 208 through 214 while the PAPR 100 is powered on. In an embodiment, the processing of blocks 208, 210, 212, and 214 may be iterated at some periodic rate, for example once per minute, once per second, ten times per second, or some other periodic rate. In an embodiment, the processing of blocks 208, 210, 212, and 214 are performed by the controller 110. In an embodiment, the processing of block 206 is also performed at least in part by the controller 110.

Figure 3:
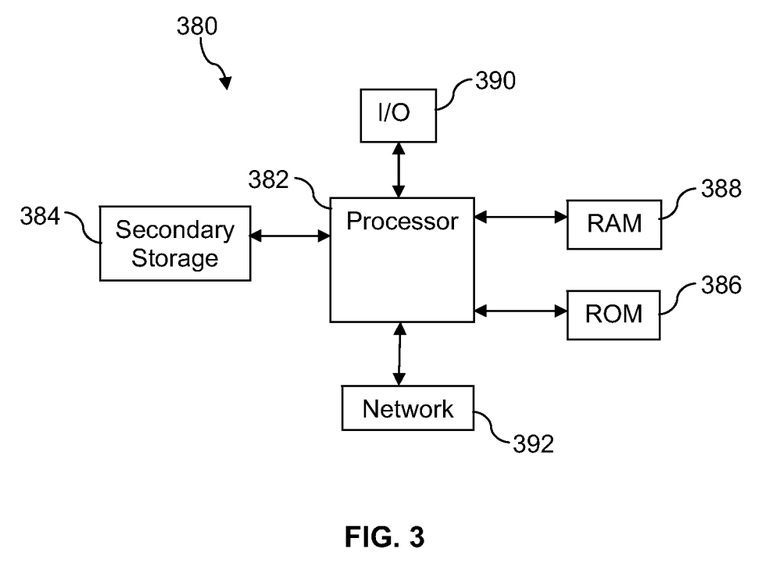
FIG. 3 is an illustration of an exemplary computer system suitable for implementing an embodiment of the disclosure.

FIG. 3 illustrates a computer system 380 suitable for implementing one or more embodiments disclosed herein. For example the combination of the controller 110, the oxygen sensor 114, the alarm device 120, and the event store 130 may share some of the structures of the computer system 380. In an embodiment, the functionality described above and attributed to the controller 110 may be implemented in firmware as an algorithm that is repeatedly executed on a processor 382 of the computer system 380. In an embodiment, the computer system 380 comprises the processor 382 (which may be referred to as a central processor unit or CPU) that is in communication with memory devices including secondary storage 384, read only memory (RUM) 386, random access memory (RAM) 388, input/output (I/O) devices 390, and network connectivity devices 392. The processor 382 may be implemented as one or more CPU chips. In some embodiments, the computer system 380 may not comprise all of the components enumerated above. For example, in an embodiment, the computer system 380 may not have secondary storage 384. Additionally, some of the components listed separately above may be combined in a single component, for example the processor 382, the ROM 386, and the RAM 388 may be integrated in a single component and/or single semiconductor chip.

It is understood that by programming and/or loading executable instructions onto the computer system 380, at least one of the CPU 382, the RAM 388, and the ROM 386 are changed, transforming the computer system 380 in part into a particular machine or apparatus having the novel functionality taught by the present disclosure. It is fundamental to the electrical engineering and software engineering arts that functionality that can be implemented by loading executable software into a computer be converted to a hardware implementation by well known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

The secondary storage 384 is typically comprised of one or more disk drives or tape drives and is used for non-volatile storage of data and as an over-flow data storage device if RAM 388 is not large enough to hold all working data. Secondary storage 384 may be used to store programs which are loaded into RAM 388 when such programs are selected for execution. The ROM 386 is used to store instructions and perhaps data which are read during program execution. ROM 386 is a non-volatile memory device which typically has a small memory capacity relative to the larger memory capacity of secondary storage 384. The RAM 388 is used to store volatile data and perhaps to store instructions. Access to both RUM 386 and RAM 388 is typically faster than to secondary storage 384. The secondary storage 384, the RAM 388, and/or the ROM 386 may be referred to in some contexts as computer readable storage media and/or non-transitory computer readable media.

The event store 130 above with reference to FIG. 1 may be part of the ROM 386 or the RAM 388. Likewise, if an altitude parameter is configured into the PAPR 100, the altitude parameter may be stored in the RUM 386 and/or in the RAM 388. In an embodiment, power on of the PAPR 100, the processor 382 reads the altitude parameter from the ROM 386 or the RAM 388.

I/O devices 390 may include a variety of devices, for example, the oxygen sensor 114, the alarm device 120, the indicator light 122, the aural tone generating device 124, the vibrator device 126, the visual display device 128, switches, dials, voice recognizers, and other devices.

The network connectivity devices 392 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other known network devices. These network connectivity devices 392 may enable the processor 382 to communicate with the Internet or one or more intranets. With such a network connection, it is contemplated that the processor 382 might receive information from the network, or might output information to the network in the course of performing the above-described method steps. Such information, which is often represented as a sequence of instructions to be executed using processor 382, may be received from and outputted to the network, for example, in the form of a computer data signal embodied in a carrier wave.

Such information, which may include data or instructions to be executed using processor 382 for example, may be received from and outputted to the network, for example, in the form of a computer data baseband signal or signal embodied in a carrier wave. The baseband signal or signal embedded in the carrier wave, or other types of signals currently used or hereafter developed, may be generated according to several methods well known to one skilled in the art. The baseband signal and/or signal embedded in the carrier wave may be referred to in some contexts as a transitory signal.

The processor 382 executes instructions, codes, computer programs, scripts which it accesses from hard disk, floppy disk, optical disk (these various disk based systems may all be considered secondary storage 384), ROM 386, RAM 388, or the network connectivity devices 392. While only one processor 382 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 384, for example, hard drives, floppy disks, optical disks, and/or other device, the ROM 386, and/or the RAM 388 may be referred to in some contexts as non-transitory instructions and/or non-transitory information.

In some contexts, the secondary storage 384, the ROM 386, and the RAM 388 may be referred to as a non-transitory computer readable medium or a computer readable storage media. A dynamic RAM embodiment of the RAM 388, likewise, may be referred to as a non-transitory computer readable medium in that while the dynamic RAM receives electrical power and is operated in accordance with its design, for example during a period of time during which the computer 380 is turned on and operational, the dynamic RAM stores information that is written to it. Similarly, the processor 382 may comprise an internal RAM, an internal ROM, a cache memory, and/or other internal non-transitory storage blocks, sections, or components that may be referred to in some contexts as non-transitory computer readable media or computer readable storage media.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A powered air purifying respirator (PAPR), comprising:
   an electric motor mechanically coupled to a blower configured to draw ambient atmospheric air through one or more purifying elements for delivery to a face mask;
   an oxygen sensor configured to detect oxygen concentration level in ambient atmospheric air;
   an alarm device; and
   a controller coupled to the oxygen sensor and to the electric motor, wherein the controller controls the electric motor, wherein the controller determines if the oxygen concentration is deficient by comparing the oxygen concentration level in the ambient atmospheric air to an ambient atmospheric air oxygen deficiency threshold, wherein the ambient atmospheric air oxygen deficiency threshold is based on altitude, and wherein the controller commands the alarm device to present an indication when the oxygen concentration is deficient.

2. The PAPR of claim 1, wherein the alarm device comprises at least one of a vibrator device, an aural tone generating device, a visual display device, or a light device.

3. The PAPR of claim 1, further comprising an event store coupled to the controller, wherein the controller writes a record into the event store when it determines the oxygen concentration is deficient.

4. The PAPR of claim 1, wherein the altitude is preconfigured into the PAPR before use.

5. The PAPR of claim 1, further comprising an altitude sensor coupled to the controller, wherein the altitude is automatically determined by the controller by analyzing an indication of altitude provided by the altitude sensor, and wherein the ambient atmospheric air oxygen deficiency threshold is indexed based on the determined altitude.

6. The PAPR of claim 1, further comprising a global positioning system (GPS) receiver coupled to the controller, wherein the altitude is automatically provided to the controller by the global positioning system receiver, and wherein the ambient atmospheric air oxygen deficiency threshold is indexed based on the provided altitude.

7. The PAPR of claim 1, wherein altitude is automatically determined, and the controller automatically determines the ambient atmospheric air oxygen deficiency threshold based on the determined altitude.

8. The PAPR of claim 1, wherein at an altitude below 8000 ft. the ambient atmospheric air oxygen deficiency threshold is less than 19.5%.

9. The PAPR of claim 1, wherein the ambient atmospheric air oxygen deficiency threshold ranges from 16-19.55% based on altitude.

10. The PAPR of claim 1, wherein the oxygen concentration level in the ambient atmospheric air is sensed by the oxygen sensor.

11. A powered air purifying respirator (PAPR), comprising:
    an electric motor mechanically coupled to a blower configured to draw ambient atmospheric air for delivery to a face mask;
    an oxygen sensor configured to detect oxygen concentration level in ambient atmospheric air;
    an alarm device;
    an event store; and
    a controller coupled to the oxygen sensor, to the alarm device, to the event store, and to the electric motor, wherein the controller controls the electric motor, wherein the controller receives an indication of an oxygen concentration from the oxygen sensor, wherein the controller determines if the oxygen concentration is deficient by comparing the indication of the oxygen concentration to an ambient atmospheric air oxygen deficiency threshold, wherein the ambient atmospheric air oxygen deficiency threshold is based on altitude, wherein the controller commands the alarm device to present an indication and writes a record in the event store when it determines the oxygen concentration is deficient.

12. The PAPR of claim 11, wherein the record the controller writes in the event store comprises the indication of the oxygen concentration, wherein the record the controller writes in the event store comprises an indication of date and time at which the record is generated, wherein the controller writes only a single record to the event store for a single instance of oxygen deficiency, wherein the single instance continues until the oxygen level returns above a pre-determined level of oxygen deficiency, and wherein the controller updates the single record to capture an extreme sensed value of oxygen deficiency during the single instance of oxygen deficiency.

13. The PAPR of claim 12, wherein the record the controller writes in the event store comprises an indication of an identity of a user of the PAPR.

14. The PAPR of claim 11, wherein the alarm device presents at least one of a vibration indication, an aural tone indication, or a visible indication.

15. A powered air purifying respirator (PAPR), comprising:
an electric motor mechanically coupled to a blower configured to draw ambient atmospheric air through one or more purifying elements for delivery to a face mask;
an oxygen sensor configured to detect oxygen concentration level in ambient atmospheric air;
an alarm device;
an event store; and
a controller coupled to the oxygen sensor, to the alarm device, to the event store, and to the electric motor, wherein the controller controls the electric motor, wherein the controller receives an indication of an oxygen concentration from the oxygen sensor and determines if the oxygen concentration is deficient by comparing the indication of the oxygen concentration to an ambient atmospheric air oxygen deficiency threshold, wherein the ambient atmospheric air oxygen deficiency threshold is based on altitude, and wherein, when the controller determines the oxygen concentration is deficient, the controller commands the alarm device to present an indication of the oxygen deficiency and writes a record in the event store.

16. The PAPR of claim 15, wherein the altitude is pre-configured into the PAPR before use.

17. The PAPR of claim 15, further comprising an altitude sensor coupled to the controller, wherein the altitude is determined by the controller by analyzing an indication of altitude provided by the altitude sensor.

18. The PAPR of claim 15, further comprising a global positioning system (GPS) receiver coupled to the controller, wherein the altitude is provided to the controller by the global positioning system receiver.

19. The PAPR of claim 15, wherein the record the controller writes in the event store comprises the indication of the oxygen concentration.

20. The PAPR of claim 19, wherein the record the controller writes in the event store comprises an indication of date and time at which the record is generated, and wherein the controller writes at least one oxygen deficiency record for each instance of oxygen deficiency, wherein each instance of oxygen deficiency continues until the oxygen concentration is no longer deficient.

* * * * *

UNITED STATES PATENT AND TRADEMARK OFFICE
CERTIFICATE OF CORRECTION

PATENT NO.          : 9,808,656 B2
APPLICATION NO.     : 13/346340
DATED               : November 7, 2017
INVENTOR(S)         : Vinay Kumar Vinnakota, Praveen Kumar Palacharla and Swapnil Gopal Patil It is certified that error appears in the above-identified patent and that said Letters Patent is hereby corrected as shown below:

In the Specification

Column 4, Line 42: "ones" should be "tones"

Column 7, Line 38: "RUM" should be "ROM"

Column 8, Line 27: "RUM" should be "ROM"

Column 8, Line 35: "RUM" should be "ROM"

In the Claims

Column 10, Line 41: "19.55" should be "19.5"

Signed and Sealed this
Sixth Day of March, 2018

Andrei Iancu
*Director of the United States Patent and Trademark Office*